US00PP16144P2

(12) United States Plant Patent
Lander

(10) Patent No.: US PP16,144 P2
(45) Date of Patent: Dec. 6, 2005

(54) ***PETUNIA* PLANT NAMED 'LANBOR'**

(50) Latin Name: *Petunia×hybrida*
Varietal Denomination: Lanbor

(76) Inventor: Kenneth Lander, P.O. Box 403, Pugwash, N.S. (CA), B0K-1L0

( * ) Notice: Subject to any disclaimer, the term of this patent is extended or adjusted under 35 U.S.C. 154(b) by 21 days.

(21) Appl. No.: 10/955,391

(22) Filed: Sep. 30, 2004

(51) Int. Cl.[7] ..... A01H 5/00

(52) U.S. Cl. ..... Plt./356
(58) Field of Search ..... Plt./356

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Petunia* plant named 'Lanbor', characterized by its cascading plant habit; freely branching habit; freely and continuous flowering habit; numerous single flowers that are light purple in color with dark purple-colored centers; good garden performance; and resistance to Powdery Mildew.

1 Drawing Sheet

Botanical classification/cultivar designation: *Petunia×hybrida* cultivar Lanbor.

BACKGROUND OF THE INVENTION

The present Invention relates to a new and distinct cultivar of *Petunia* plant, botanically known as *Petunia×hybrida*, and hereinafter referred to by the cultivar name Lanbor.

The new *Petunia* is a product of a planned breeding program conducted by the Inventor in West Pugwash, Nova Scotia, Canada. The objective of the breeding program is to create new disease-resistant *Petunias* with cascading plant habit and attractive flower colors.

The new *Petunia* originated from a cross-pollination made by the Inventor in March, 2001 of an unnamed seedling selection of *Petunia×hybrida*, not patented, as the female, or seed parent, with an unnamed seedling selection of *Petunia×hybrida*, not patented, as the male, or pollen parent. The new *Petunia* was discovered and selected as a single plant from the resulting progeny of the stated cross-pollination in June, 2001 in West Pugwash, Nova Scotia, Canada, on the basis of its plant habit and attractive flower coloration.

Asexual reproduction of the new cultivar by terminal vegetative cuttings since June, 2001, in West Pugwash, Nova Scotia, Canada has shown that the unique features of this new *Petunia* are stable and reproduced true to type in successive generations.

SUMMARY OF THE INVENTION

Plants of the cultivar Lanbor have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Lanbor'. These characteristics in combination distinguish 'Lanbor' as a new and distinct cultivar:

1. Cascading plant habit.
2. Freely branching habit.
3. Freely and continuous flowering habit.

4. Numerous single flowers that are light purple in color with dark purple-colored centers.
5. Good garden performance.
6. Resistant to Powdery Mildew.

In side-by-side comparisons conducted in West Pugwash, Nova Scotia, Canada, plants of the new *Petunia* differed from plants of the female parent selection in the following characteristics:

1. Plants of the new *Petunia* were not as vigorous as plants of the female parent selection.
2. Plants of the new *Petunia* and the female parent selection differed in flower coloration.
3. Plants of the new *Petunia* were resistant to Powdery Mildew whereas plants of the female parent selection were not resistant to Powdery Mildew.

In side-by-side comparisons conducted in West Pugwash, Nova Scotia, Canada, plants of the new *Petunia* differed from plants of the male parent selection in the following characteristics:

1. Plants of the new *Petunia* were more compact than plants of the male parent selection.
2. Plants of the new *Petunia* had smaller flowers than plants of the male parent selection.

Plants of the new *Petunia* can be compared to plants of the cultivar Surfinia Blue Vein, not patented. In side-by-side comparisons conducted in West Pugwash, Nova Scotia, Canada, plants of the new *Petunia* differed from plants of the cultivar Surfinia Blue Vein in the following characteristics:

1. Plants of the new *Petunia* were more uniform and not as vigorous as plants of the cultivar Surfinia Blue Vein.
2. Plants of the new *Petunia* and the cultivar Surfina Blue Vein differed in flower coloration.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia*.

The photograph at the top of the sheet is a close-up view of typical flowers and leaves of 'Lanbor'.

The photograph at the bottom of the sheet comprises a side perspective view of a typical plant of 'Lanbor' grown in a container.

DETAILED BOTANICAL DESCRIPTION

The aforementioned photographs and following observations and measurements describe plants grown in Bonsall, Calif., in an outdoor nursery during the spring and summer under full sun conditions with day temperatures ranging from about 16 to about 32° C. and night temperatures ranging from about 10 to about 18° C. After planting rooted cuttings, plants were grown for about eight weeks in 12.5-cm containers with three plants per container. Color references are made to The Royal Horticultural Society Colour Chart, 1995 Edition, except where general terms of ordinary dictionary significance are used.

Botanical classification: *Petunia×hybrida* cultivar Lanbor.

Parentage:

*Female parent.*—Unnamed seedling selection of *Petunia×hybrida*, not patented.

*Male parent.*—Unnamed seedling selection of *Petunia×hybrida*, not patented.

Propagation:

*Type cutting.*—Terminal vegetative cuttings.

*Time to initiate roots, summer.*—About 10 days at 20° C.

*Time to initiate roots, winter.*—About 17 days at 24° C.

*Time to develop roots, summer.*—About 17 days at 20° C.

*Time to develop roots, winter.*—About 27 days at 24° C.

*Root description.*—Fine; white, close to 155D, in color.

*Rooting habit.*—Freely branching.

Plant description:

*Form.*—Annual flowering plant; indeterminate; initially upright, then low-trailing to cascading plant habit; uniformly mounded plant form. Freely branching habit with about four lateral branches and five to six secondary lateral branches per plant.

*Usage.*—Appropriate for hanging baskets, window boxes, patio containers and landscape applications.

*Plant height.*—About 16 cm.

*Plant diameter.*—About 48 cm.

*Vigor.*—Vigorous; moderate to rapid growth rate.

*Lateral branches.*—Length: About 30 cm. Diameter: About 3 mm. Internode length: About 2 cm. Texture: Pubescent; viscid. Color: 144A.

*Foliage description.*—Arrangement: Alternate before flowering; opposite after flowers develop; simple. Length: About 5 cm. Width: About 3.1 cm. Shape: Elliptic. Apex: Broadly acute to nearly rounded. Base: Attenuate. Margin: Entire. Texture, upper and lower surfaces: Sparsely pubescent; glandular; slightly rough. Venation pattern: Pinnate, arcuate. Color: Developing and fully expanded leaves, upper surface: 146A. Developing and fully expanded leaves, lower surface: 146B. Venation, upper and lower surfaces: 146C. Petiole length: About 6 mm. Petiole diameter: About 4 mm. Petiole texture, upper and lower surfaces: Pubescent. Petiole color, upper and lower surfaces: 146C.

Flower description:

*Flower type and habit.*—Single salverform flowers; flowers face mostly upward or outward; axillary. Freely flowering habit, about ten open flowers and about 18 flower buds per lateral branch at one time.

*Natural flowering season.*—Long day responsive; long flowering period, spring until frost in the autumn; flowering continuous during this period. Plants start flowering about four to six weeks after planting rooted cuttings. Flowers persistent.

*Flower longevity on the plant.*—About five to seven days.

*Fragrance.*—Faint; sweet.

*Flower size.*—Diameter: About 5.8 cm. Depth: About 6 cm. Tube length: About 3.6 cm. Throat diameter, distal end: About 1.5 cm. Tube diameter, proximal end: About 3 mm.

*Flower buds.*—Length: About 4.4 cm. Diameter: About 7 mm. Shape: Elongated oblong with ruffled apices. Color: 187A.

*Petals.*—Quantity/arrangement: About five petals fused in a single whorl, funnelform. Length from throat: About 2.6 cm. Width: About 2.8 cm. Shape: Roughly fan-shaped. Apex: Rounded with shallow central point. Margin: Entire, very slightly serrate. Texture, upper and lower surfaces: Smooth, satiny. Texture, throat: Smooth, velvety. Texture, tube: Pubescent. Color: When opening, upper surface: 77C. When opening, lower surface: 77C to 77D. Fully opened, upper surface: 77D; color becoming closer to 75C with development. Fully opened, lower surface: 75A. Flower throat (inside): 79A. Flower tube (outside): 79A to 79B. Venation, upper petal surface: 79B. Venation, lower petal surface: 79D. Venation, throat: 79A. Venation, tube: 186A.

*Sepals.*—Arrangement/appearance: Single whorl of five sepals fused at base, star-shaped. Length: About 1.2 cm. Width: About 3 mm. Shape: Linear, strap-like. Apex: Rounded. Margin: Entire. Texture, upper and lower surfaces: Pubescent. Color, upper and lower surfaces: 146A.

*Peduncles.*—Length: About 3.8 to 5 cm. Width: About 2 mm. Angle: About 45 to 60° from the stem. Strength: Strong. Texture: Pubescent. Color: 144A.

*Reproductive organs.*—Stamens: Quantity per flower: About five. Anther shape: Ovoid. Anther length: About 2 mm. Anther color: 198C. Pollen amount: Moderate. Pollen color: More blue than 202B. Pistils: Quantity per flower: One. Pistil length: About 2.5 cm. Style length: About 1.9 cm. Style color: 77C to 77D. Stigma shape: Anvil-shaped. Stigma color: 148A. Ovary color: 144C.

*Seed/fruit.*—Seed and/or fruit production has not been observed.

Disease/pest resistance: Plants of the new *Petunia* have been noted to be resistant to Powdery Mildew. Plants of the new *Petunia* have not been noted to be resistant to other pathogens and pests common to *Petunias*.

Garden performance: Plants of the new *Petunia* have been observed to have good garden performance. Plants of the new *Petunia* have been noted to tolerate temperatures from −2 to 40° C. and have excellent tolerance to rain and wind.

It is claimed:

1. A new and distinct cultivar of *Petunia* plant named 'Lanbor', as illustrated and described.

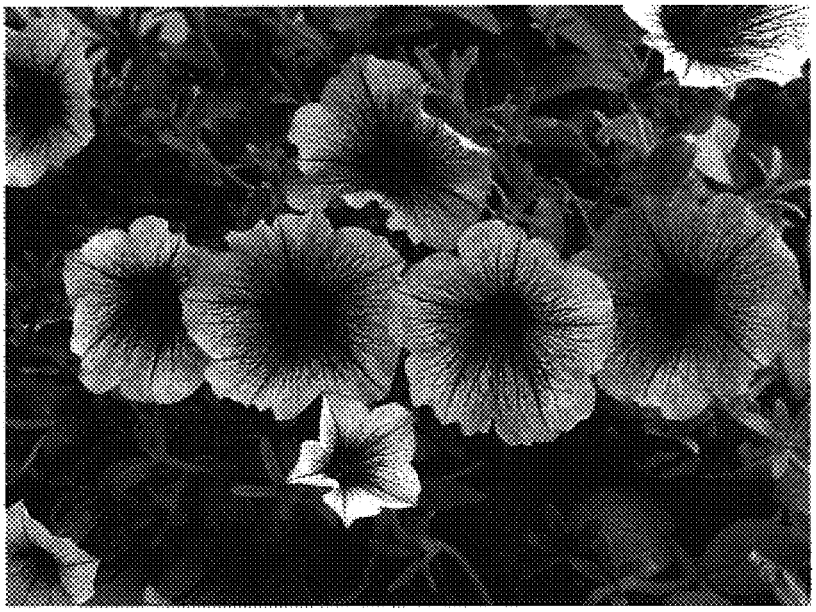
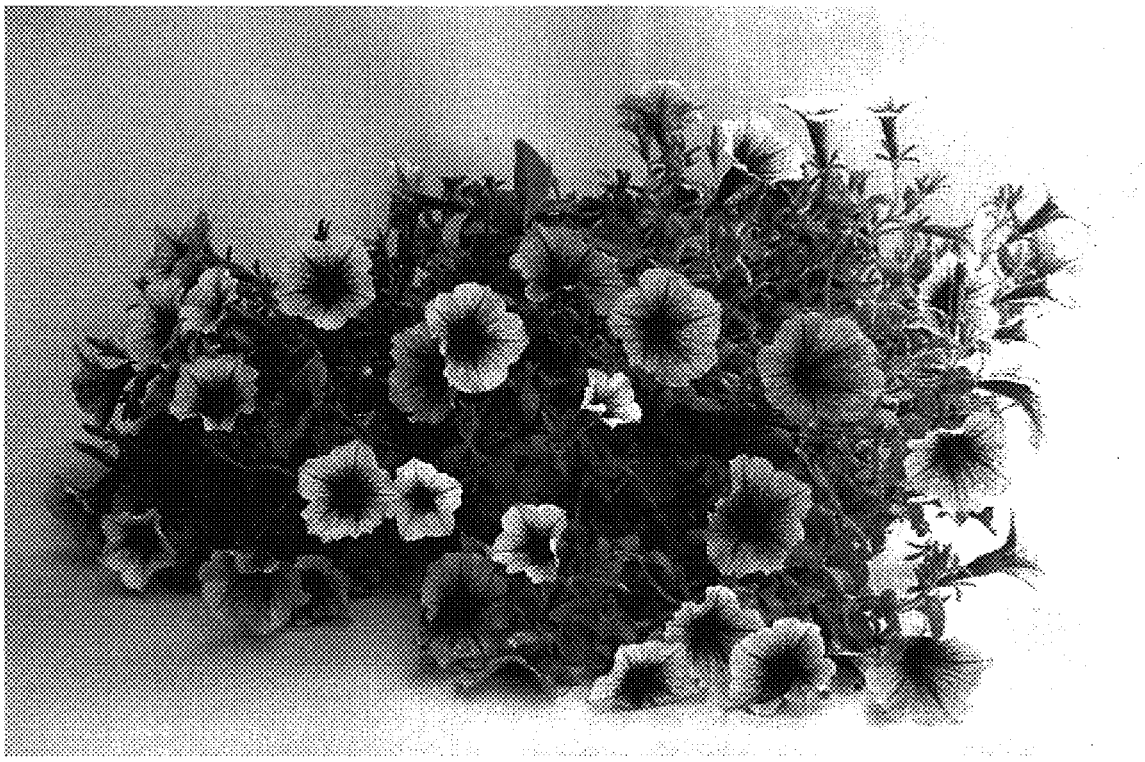

* * * * *